US012642466B2

(12) United States Patent (10) Patent No.: US 12,642,466 B2
Welch et al. (45) Date of Patent: Jun. 2, 2026

(54) DEVICES FOR SECURELY STORING BODILY FLUIDS AND ASSOCIATED SYSTEMS AND METHODS

(71) Applicant: INNOVERO LLC, Colorado Springs, CO (US)

(72) Inventors: Emily Welch, Seattle, WA (US); Erwin Berthier, Seattle, WA (US); Ben Casavant, Seattle, WA (US); Jake Myre, Seattle, WA (US); Bryce Petersen, Seattle, WA (US); Arna Ionescu Stoll, Seattle, WA (US)

(73) Assignee: INNOVERO, LLC, Colorado Springs, CO (US)

( * ) Notice: Subject to any disclaimer, the term of this patent is extended or adjusted under 35 U.S.C. 154(b) by 695 days.

(21) Appl. No.: 17/919,669

(22) PCT Filed: Apr. 26, 2021

(86) PCT No.: PCT/US2021/029082
§ 371 (c)(1),
(2) Date: Oct. 18, 2022

(87) PCT Pub. No.: WO2021/222066
PCT Pub. Date: Nov. 4, 2021

(65) Prior Publication Data
US 2023/0157599 A1 May 25, 2023

Related U.S. Application Data

(60) Provisional application No. 63/025,619, filed on May 15, 2020, provisional application No. 63/015,821, filed on Apr. 27, 2020.

(51) Int. Cl.
*A61B 5/15* (2006.01)
*A61B 5/151* (2006.01)
*B01L 9/06* (2006.01)

(52) U.S. Cl.
CPC .... *A61B 5/150343* (2013.01); *A61B 5/15107* (2013.01); *B01L 9/06* (2013.01); *B01L 2300/043* (2013.01)

(58) Field of Classification Search
CPC .. A61B 5/150343; A61B 5/15107; B01L 9/06
See application file for complete search history.

(56) References Cited

U.S. PATENT DOCUMENTS

2002/0137025 A1 9/2002 Quattrocchi
2005/0015020 A1 1/2005 Levaughn et al.
(Continued)

FOREIGN PATENT DOCUMENTS

WO 2017093763 A2 6/2017
WO 2018130825 A1 7/2018

OTHER PUBLICATIONS

International Search Report and Written Opinion in PCT Application No. PCT/US2021/029082, mailed Aug. 10, 2021 (12 pages).
(Continued)

*Primary Examiner* — Daniel L Cerioni
(74) *Attorney, Agent, or Firm* — Leason Ellis LLP

(57) ABSTRACT

Devices, systems, and methods for storing and/or transporting bodily fluid samples are disclosed herein. In some embodiments, a device for storing and/or transporting a sample of bodily fluid is configured to receive a collection cartridge including a housing and a sample tray removably coupled to the housing. The device can include a base and a cover pivotally coupled to the base. The cover is movable relative to the base between.an open position in which the jig portion is accessible and a closed position in which the jig portion is inaccessible. The base can include a jig portion configured to (a) receive the collection cartridge and (b) decouple the sample tray from a housing of the collection cartridge.

14 Claims, 14 Drawing Sheets

(56) References Cited

U.S. PATENT DOCUMENTS

| | | |
|---|---|---|
| 2005/0033340 A1 | 2/2005 | Lipoma et al. |
| 2011/0164245 A1 | 7/2011 | Eikelmann et al. |
| 2013/0211289 A1 | 8/2013 | Moga et al. |
| 2018/0078241 A1* | 3/2018 | Moga ............... A61B 5/150022 |
| 2020/0146606 A1* | 5/2020 | Casavant ......... A61B 5/150862 |

OTHER PUBLICATIONS

Supplementary European Search Report in EP Application No. 21797088.8-1014/4142590, mailed Jul. 26, 2024 (13 pages).

* cited by examiner

100

104          106          112

102          110

100          106          112

104

102          110

452                                                    330

452

454

"SNAP!"

DEVICES FOR SECURELY STORING BODILY FLUIDS AND ASSOCIATED SYSTEMS AND METHODS

CROSS-REFERENCE TO RELATED APPLICATIONS

This application is a U.S. National Phase Application under 35 U.S.C. § 371 of International Patent Application No. PCT/US2021/029082, filed on Apr. 26, 2021, which claims the benefit of U.S. Provisional Patent Application No. 63/015,821, filed Apr. 27, 2020, and titled "DEVICES FOR SECURELY STORING BODILY FLUIDS AND ASSOCIATED SYSTEMS AND METHODS," and U.S. Provisional Patent Application No. 63/025,619, filed May 15, 2020, and titled "DEVICES FOR SECURELY STORING BODILY FLUIDS AND ASSOCIATED SYSTEMS AND METHODS," each of which is incorporated herein by reference in its entirety.

TECHNICAL FIELD

The present technology is related to the collection of bodily fluids and their delivery and storage in removable containers and, more particularly, to devices for securely storing and/or transporting removable containers containing bodily fluids.

BACKGROUND

Devices, systems, and methods to collect bodily fluids are necessary for the growing field of personalized medicine. While analysis laboratories are well suited to perform diagnostic tests, the collection of blood samples remains challenging, in particular for people that do not have simple access to a blood testing laboratory. Such people can be located in rural areas, underserved sub-urban areas, or low resource areas and have significant barriers to accessing diagnostic services. Alternatively, it is often desirable to quickly and efficiently perform blood tests for people outside the context of blood testing laboratories such as for testing athletes for the use of performance enhancing drugs. To reach test subjects in any location and connect them with blood testing facilities, robust systems for sample encapsulation, stabilization, and shipping must be developed.

BRIEF DESCRIPTION OF THE DRAWINGS

Many aspects of the present technology can be better understood with reference to the following drawings. The components in the drawings are not necessarily to scale. Instead, emphasis is placed on clearly illustrating the principles of the present technology.

DETAILED DESCRIPTION

The present technology is directed generally to devices and methods for securely storing and/or transporting samples of bodily fluid (e.g., blood) from a subject. In some embodiments, a bodily fluid collection device is used to withdraw the bodily fluid from the subject and into a cartridge releasably coupled to the collection device. The cartridge can include a housing and a sample tray releasably coupled to the housing. The sample tray can include a plurality of collectors configured to receive and store a portion of the bodily fluid (e.g., a selected volume of the bodily fluid). In some embodiments, the collection cartridge can be removed from the collection device after the bodily fluid is withdrawn, and then positioned within a case for secure storage and/or transport to a remote testing facility or other location. The case can include a base and a cover pivotally coupled to the base such that the case can be opened and closed. The base can include a jig portion configured to (a) receive the cartridge and (b) decouple the sample tray from the housing of the cartridge. In some embodiments, the case can include features that inhibit tampering with the bodily fluid sample stored in the collection cartridge.

Specific details of several embodiments of the present technology are described herein with reference to FIGS. 1A-7D. However, the present technology may be practiced without some of these specific details. In some instances, well-known structures and techniques often associated with bodily fluid collection devices, collection cartridges, etc., have not been shown in detail so as not to obscure the present technology. The terminology used in the description presented below is intended to be interpreted in its broadest reasonable manner, even though it is being used in conjunction with a detailed description of certain specific embodiments of the disclosure. Certain terms may even be emphasized below: however, any terminology intended to be interpreted in any restricted manner will be overtly and specifically defined as such in this Detailed Description section.

The accompanying Figures depict embodiments of the present technology and are not intended to be limiting of its scope. The sizes of various depicted elements are not necessarily drawn to scale, and these various elements may be arbitrarily enlarged to improve legibility. Component details may be abstracted in the Figures to exclude details such as position of components and certain precise connections between such components when such details are unnecessary for a complete understanding of how to make and use the present technology. Many of the details, dimensions, angles, and other features shown in the Figures are merely illustrative of particular embodiments of the disclosure. Accordingly, other embodiments can have other details, dimensions, angles, and features without departing from the spirit or scope of the present technology.

Figure 1A:
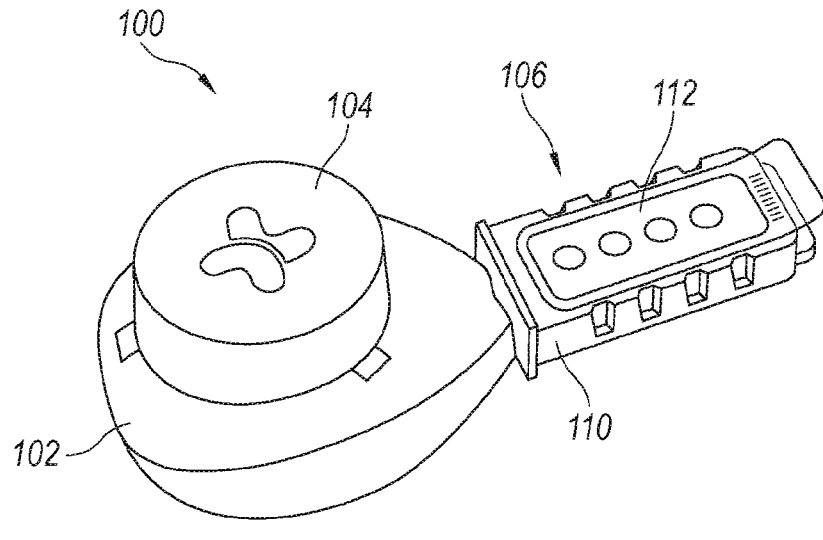
FIG. 1A is a perspective view of a bodily fluid collection device configured in accordance with embodiments of the present technology.
Figure 1B:
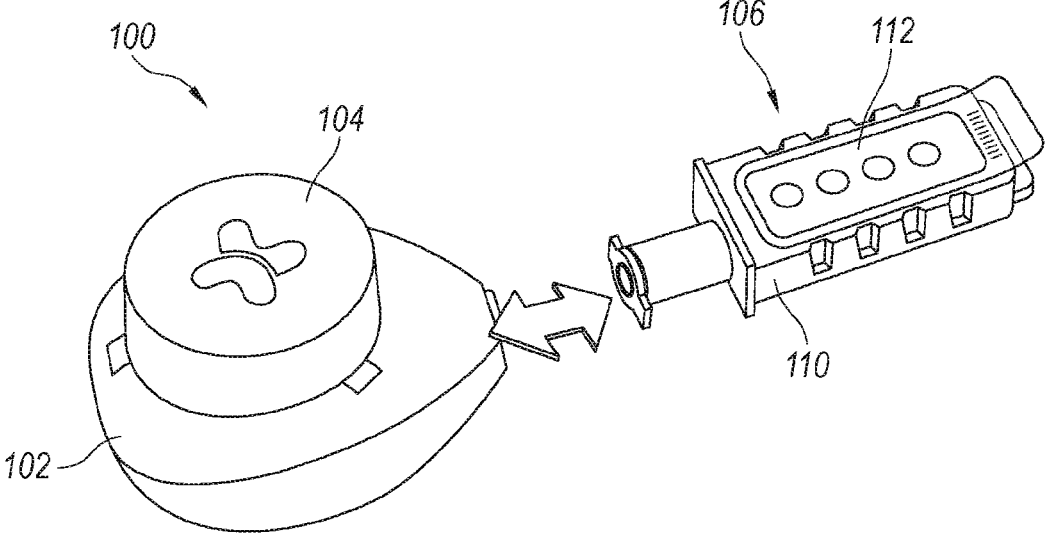
FIG. 1B is a perspective view illustrating detachment of a collection cartridge from the bodily fluid collection device in accordance with embodiments of the present technology.

FIG. 1A is a perspective view of a bodily fluid collection device 100 ("device 100") configured in accordance with embodiments of the present technology. FIG. 1B is a perspective view illustrating detachment of a collection cartridge 106 from the device 100 in accordance with embodiments of the present technology. Referring to FIGS. 1A and 1B together, the device 100 can be handheld with a size that is easily grasped and manipulated by one or both hands of a user (e.g., a patient, technician, nurse, doctor, etc.). Such handheld devices can advantageously allow the user to collect a bodily fluid sample (e.g., a blood sample) without assistance from another individual. In some embodiments, the device 100 can be operated by a layperson outside of a medical setting and without the aid of a medical professional. For example, the device 100 can be used at the home of a patient/subject, in a field clinic, onsite at a sporting event, etc.

In the illustrated embodiment, the device 100 includes a housing 102 and an actuator 104. The actuator 104 (e.g., a button) can be movable relative to the housing 102 to actuate/initiate withdrawal of a bodily fluid from the user. The housing 102 can be removably coupled to the collection cartridge 106 (e.g., a pod, reservoir, sample collector, etc.) for receiving the bodily fluid withdrawn from the user. In some embodiments, the device 100 can include one or more features that are generally similar or identical to the bodily fluid collection devices and fluid collection cartridges disclosed in, for example: (i) U.S. patent application Ser. No. 14/816,994, titled "DEVICES, SYSTEMS AND METHODS FOR GRAVITY-ENHANCED MICROFLUIDIC COLLECTION, HANDLING AND TRANSFERRING OF FLUIDS," and filed Aug. 3, 2015: (ii) U.S. Pat. No. 10,426,390, titled "DEVICES, SYSTEMS AND METHODS FOR ACTUATION AND RETRACTION IN FLUID COLLECTION," and filed Dec. 21, 2016: (iii) U.S. patent application Ser. No. 15/711,746, titled "METHODS FOR DELIVERY OF BODILY FLUIDS ONTO A FIBROUS SUBSTRATE," and filed Sep. 21, 2017; and/or (iv) U.S. Provisional Patent Application No. 62/923,379, and filed Oct. 18, 2019, each of which is incorporated herein by reference in its entirety.

The cartridge 106 can act as a removable and standardized container for bodily fluids that can be detached and used in clinical and laboratory equipment or workflows (e.g., for diagnostics and/or biomarker detection). In the illustrated embodiment, for example, the cartridge 106 includes a housing 110 and a sample tray 112 configured to collect one or more samples of the bodily fluid. In some embodiments, the sample tray 112 can be releasably coupled to the housing 110 such that that sample tray 112 can be detached from the housing 110.

Figure 2A:
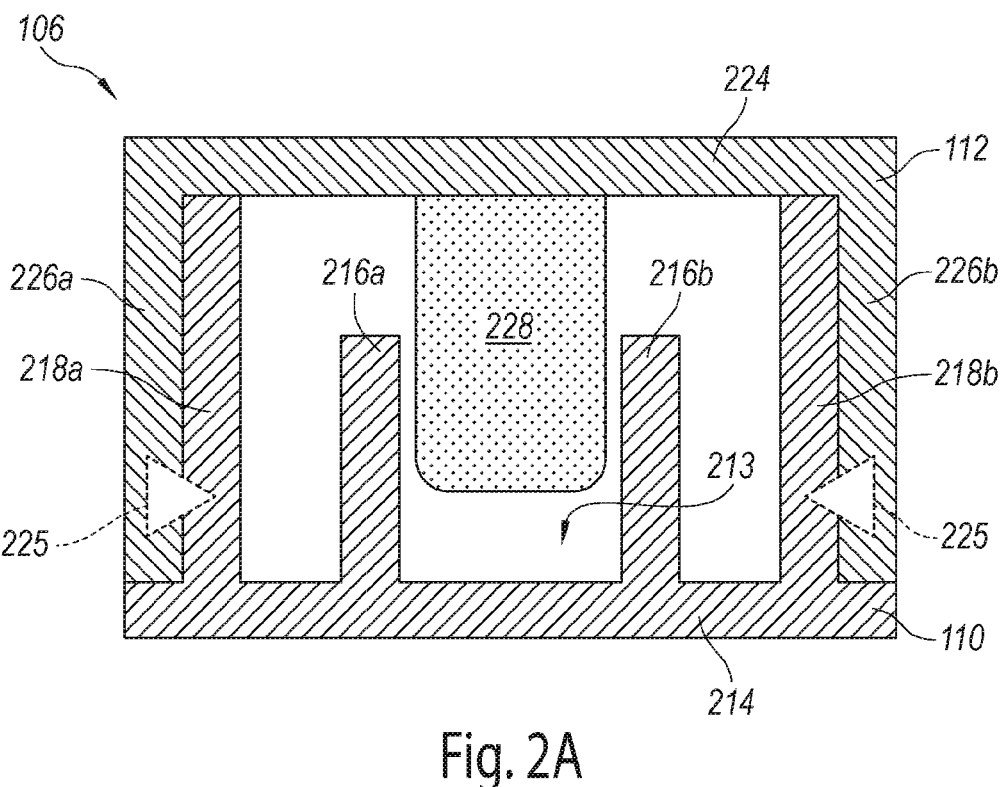
FIG. 2A is a cross-sectional side view of the collection cartridge of FIGS. 1A and 1B configured in accordance with embodiments of the present technology.
Figure 2B:
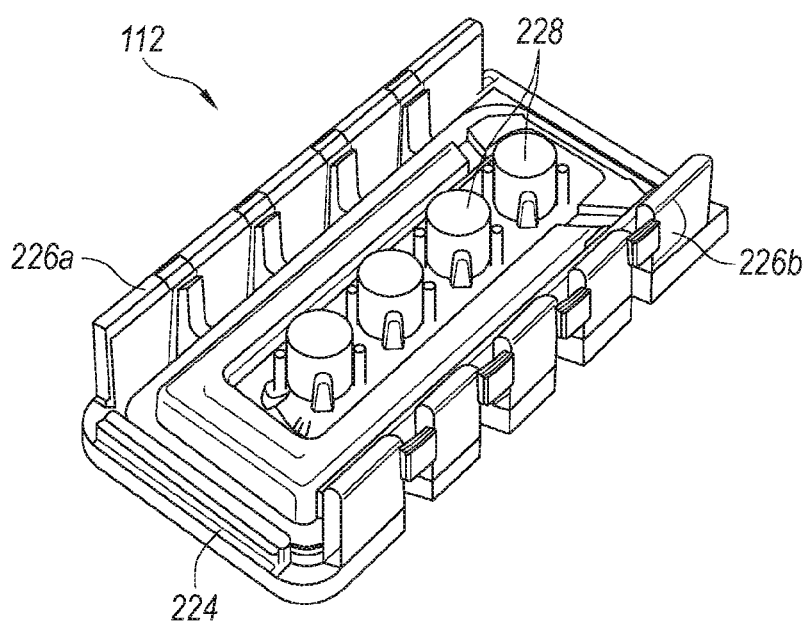
FIG. 2B is a perspective view of a sample tray of the collection cartridge detached from a housing of the collection cartridge in accordance with embodiments of the present technology.

FIG. 2A, for example, is a cross-sectional side view of the collection cartridge 106, and FIG. 2B is a perspective view of the sample tray 112 detached from the housing 110 in accordance with embodiments of the present technology.

Referring to FIGS. 2A and 2B together, in the illustrated embodiment the housing 110 includes (i) a base 214, (ii) a pair of inner sidewalls 216 (identified individually as a first inner sidewall 216a and a second inner sidewall 216b) projecting from the base 214 (e.g., perpendicular to the base 214) and together defining a fluid channel 213, and (iii) a pair of outer sidewalls 218 (identified individually as a first outer sidewall 218a and a second outer sidewall 218b) projecting from base 214. The sample tray 112 can include a base 224 and a pair of sidewalls 226 (identified individually as a first sidewall 226a and a second sidewall 226b) projecting from the base 224. In the illustrated embodiment, the sample tray 112 further includes a plurality of collectors 228 attached to (e.g., releasably coupled to) the base 224. The collectors 228 are configured to absorb and store a portion of the bodily fluid moving/flowing through the fluid channel 213. In some embodiments, the collectors 228 can comprise a plastic, paper, or other suitably absorbent material. In some embodiments, the collectors 228 are configured to absorb and store a predetermined volume of bodily fluid. In some embodiments, the collectors 228 are releasably coupled to the sample tray 112 such that the collectors 228 can be removed for testing of bodily fluid collected therein.

When the sample tray 112 is coupled to the housing 110 as shown in FIG. 2A, the sample tray 112 encloses/covers the fluid channel 213 and the collectors 228 project at least partially into the fluid channel 213. In some embodiments, the sample tray 112 can be securely coupled to the housing 110 via one or more mating features 225 (shown schematically in FIG. 2A). The mating features 225 can be, for example, correspondingly-shaped portions of the sidewalls 226 of the sample tray 112 and the outer sidewalls 218 of the housing 110, snap-fit features, magnets, adhesives, etc.

Referring to FIGS. 1A-2B together, to collect a bodily fluid sample, the device 100 is applied to a user's body, with a bottom surface of the housing 102 positioned against the skin of the user and the actuator 104 positioned away from the skin. Actuating (e.g., pressing, twisting, pulling, etc.) the actuator 104 deploys a skin-piercing feature (e.g., a blade, lancet, etc.) from within the device 100 to pierce the skin of the user. In some embodiments, the device 100 is configured to generate a vacuum within the device 100 that acts against the user's skin either directly or indirectly, and before and/or after deployment of the skin-piercing feature. Bodily fluid from the resulting incision is withdrawn into the housing 102 and collected into the cartridge 106. More specifically, the bodily fluid can be transferred from the housing 102 and into the fluid channel 213 of the cartridge 106 where it is absorbed by one or more of the collectors 228. Once a desired amount of the bodily fluid has been collected into the cartridge 106, the device 100 is removed from the skin of the user.

In some embodiments, the cartridge 106 can then be detached from the housing 102 (e.g., as shown in FIG. 2B) and stored and/or transported for subsequent testing of the bodily fluid collected in the collectors 228. In some instances, it may be desirable to store the cartridge 106 and/or the collectors 228 in a secure manner that inhibits tampering and/or contamination of the collected sample. For example, when the device 100 is used to collect a blood sample to test for illegal or prohibited drugs (e.g., in an athletic setting testing for doping agents, for employee drug screening, etc.), it is often desirable to secure the collected sample to ensure that the test is accurate by inhibiting intentional and/or unintentional tampering with the sample.

Figure 3A:
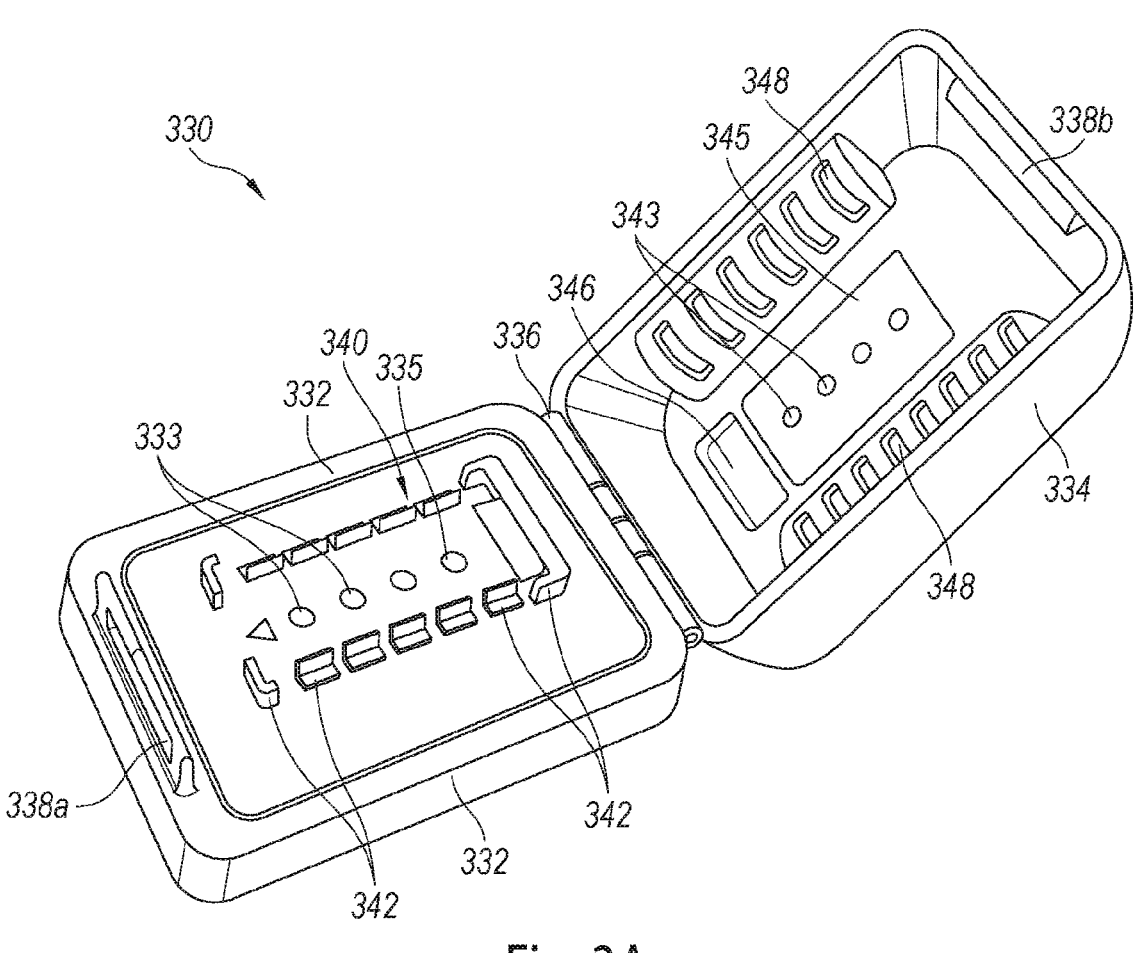
FIGS. 3A and 3B are isometric views of a case in an open position and a closed position, respectively, for securely storing and/or transporting the cartridge of FIGS. 1A-2B in accordance with embodiments of the present technology.
Figure 3B:
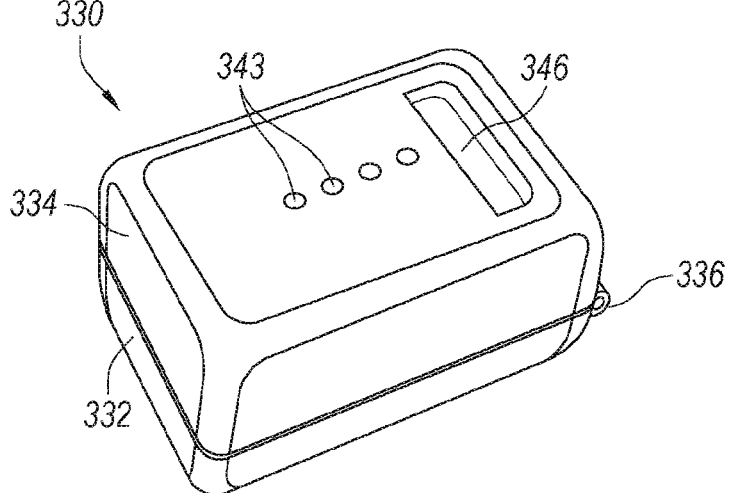

FIGS. 3A and 3B are isometric views of a case 330 in an open position and a closed position, respectively, for securely storing and/or transporting the cartridge 106 of FIGS. 1A-2B in accordance with embodiments of the present technology. Referring to FIGS. 3A and 3B together, in the illustrated embodiment the case 330 includes a base portion 332 and a cover portion 334 coupled to the base portion 332 via a hinge 336. In the open position shown in FIG. 3A, the cover portion 334 is pivoted away from the base portion 332 to, for example, allow the cartridge 106 to be inserted into and/or removed from the case 330. In the closed position shown in FIG. 3B, the cover portion 334 engages the base portion 332 (e.g., engages a perimeter of the base portion 332). In some embodiments, the base portion 332 and the cover portion 334 sealingly (or generally sealingly) engage one another in the closed position to define a sealed interior of the case 330.

In some embodiments, the base portion 332 and the cover portion 334 each include a snap lock portion 338 (identified individually as a first snap lock portion 338a and a second snap lock portion 338b) configured to engage/mate together in the closed position to secure the cover portion 334 to/over the base portion 332. In some embodiments, the snap lock portions 338 are configured to lock to one another in the closed position such that the case 330 cannot be opened, thereby inhibiting tampering with and/or contamination of a sample of bodily fluid stored in the cartridge 106 within the case 330. In other embodiments, the base portion 332 and/or the cover portion 334 can have other types of engagement/mating features for securing the base portion 332 to the cover portion 334 in the closed position. In the illustrated embodiment, the base portion 332 and the cover portion 334 each have a generally rectangular shape while, in other embodiments, the base portion 332 and/or the cover portion 334 can have other shapes (e.g., circular, oval, rectilinear, polygonal, irregular, etc.).

In the illustrated embodiment, the base portion 332 includes a jig portion 340 configured to receive and secure the cartridge 106 (FIGS. 1A-2B). With reference to FIGS. 1A-3A together, for example, the jig portion 340) can include a plurality of jig features 342 configured to engage the housing 110 of the cartridge 106 to secure the cartridge to/against the base portion 332. In some embodiments, the jig portion 340 is configured (e.g., shaped, sized, and/or positioned) such that pushing the cartridge 106 into/against the jig portion 340 decouples the sample tray 112 of the cartridge 106 from the housing 110. For example, pressing the cartridge 106 into the jig portion 340 can disengage/release the mating features 225 of the cartridge 106, thereby permitting the sample tray 112 to move relative to the housing 110. In some embodiments, the case 330 is configured (e.g., sized and shaped) such that moving the case 330 from the open position to the closed position pushes/depresses the cartridge 106 into/against the jig portion 340 to decouple the sample tray 112 from the housing 110. In other embodiments, the jig portion 340 can be omitted.

In some embodiments, (i) the base portion 332 includes a plurality of first ports 333 extending therethrough (e.g., within the jig portion 340) and (ii) the cover portion 334 includes a plurality of second ports 343 extending therethrough. The first and second ports 333, 343 can be configured such that, when the cartridge 106 is coupled to the jig portion 340 and the case 330 is in the closed position, the first and second ports 333, 343 are generally aligned with (i) one other and (ii) the collectors 228 of the sample tray 112. A user, such as a lab technician, can remove (e.g., punch out) the collectors 228 by inserting a tool through corresponding ones of the first and second ports 333, 343. In some embodiments, the case 330 can include a first sealing member 335 over the first ports 333 and a second sealing member 345 over the second ports 343. The first and second sealing members 335, 345 can be foil layers or other puncturable layers and are configured to seal the interior of the case 330 from the external environment when the case 330 is in the closed position.

In some embodiments, the cover portion 334 can include a window 346 configured to be positioned at least partially over the jig portion 340—and the cartridge 106 secured thereto—when the case 330 is in the closed position. The window 346 can facilitate inspection of the cartridge 106. In some embodiments, the case 330) can further include a desiccant 348 positioned in/on the cover portion 334 and/or the base portion 332 and configured to facilitate drying of bodily fluid collected in the cartridge 106. In other embodiments, the case 330 can include other substances, agents, etc., for producing a selected environment within the sealed interior of the case 330 when the case 330 is in the closed position.

FIGS. 4A-4H are isometric views of various stages in a method of using the case 330 to securely store and transport the cartridge 106 of FIGS. 1A-2B in accordance with embodiments of the present technology. Although features of the method illustrated in FIGS. 4A-4H are described in the context of the case 330 and the cartridge 106 described in detail above with reference to FIGS. 1A-3B, one skilled in the art will appreciate that the method can be practiced with other case designs and/or with other cartridge designs.

Figure 4A:
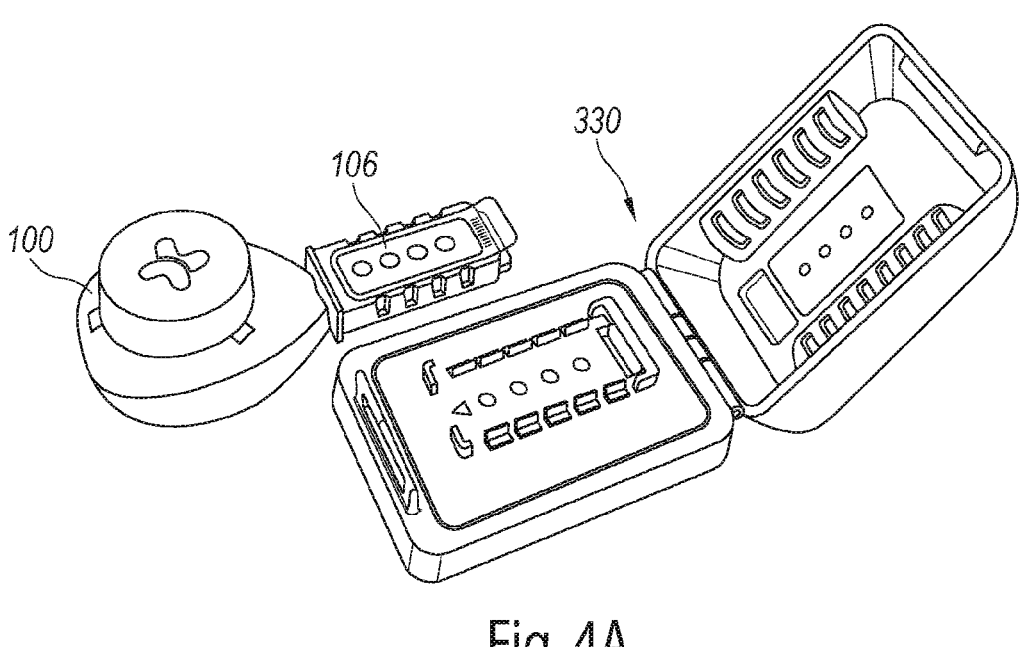
FIGS. 4A-4H are isometric views of various stages in a method of using the case of FIGS. 3A and 3B to securely store and transport the cartridge of FIGS. 1A-2B in accordance with embodiments of the present technology.
Figure 4B:
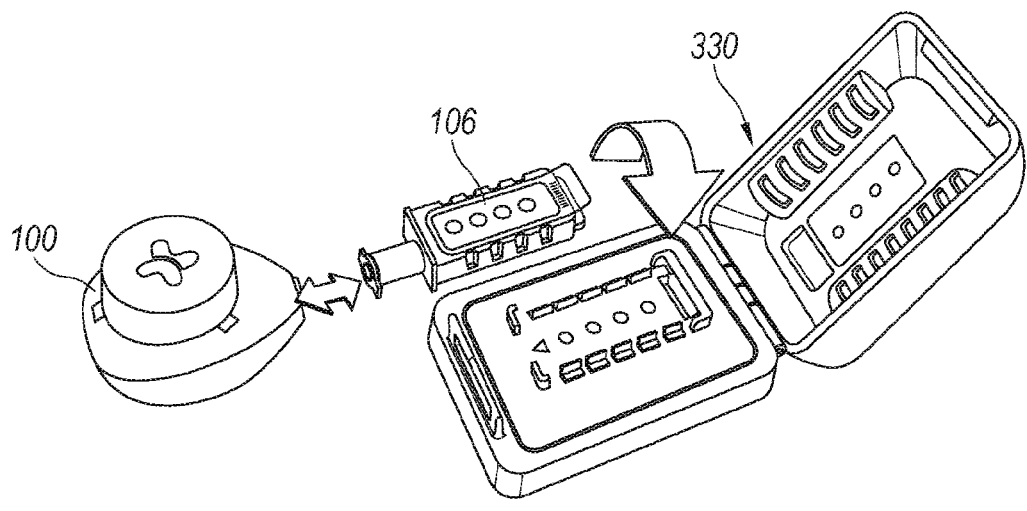

Referring first to FIG. 4A, the case 330 is moved to the open position after the device 100 is removed from a user (e.g., a patient) after sufficient bodily fluid has been collected into the cartridge 106. Next, as shown in FIG. 4B, the cartridge 106 can be detached from the device 100. In some embodiments, the device 100 is configured for single use and can therefore be discarded after the cartridge 106 is detached therefrom.

Figure 4C:
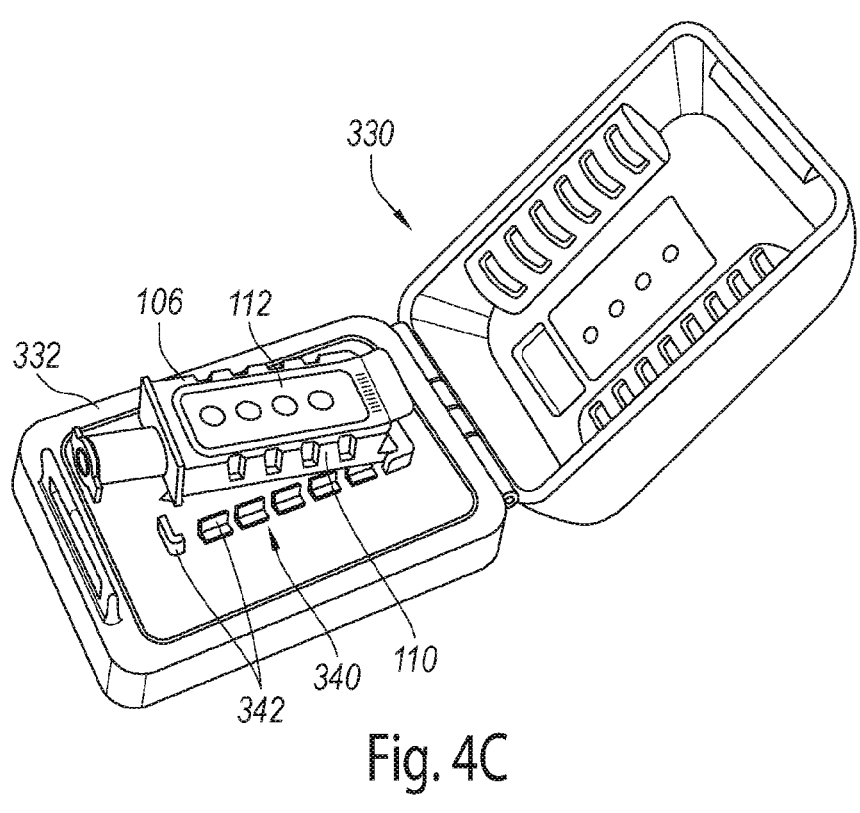

Referring next to FIG. 4C, the cartridge 106 can be positioned in/on the jig portion 340 of the base portion 332 of the case 330. Specifically, in some embodiments the housing 110 can mate with the jig features 342 to secure the cartridge 106 to base portion 332. In some embodiments, the cartridge 106 can be depressed into/against the jig portion 340 to decouple the sample tray 112 from the housing 110.

Figure 4D:
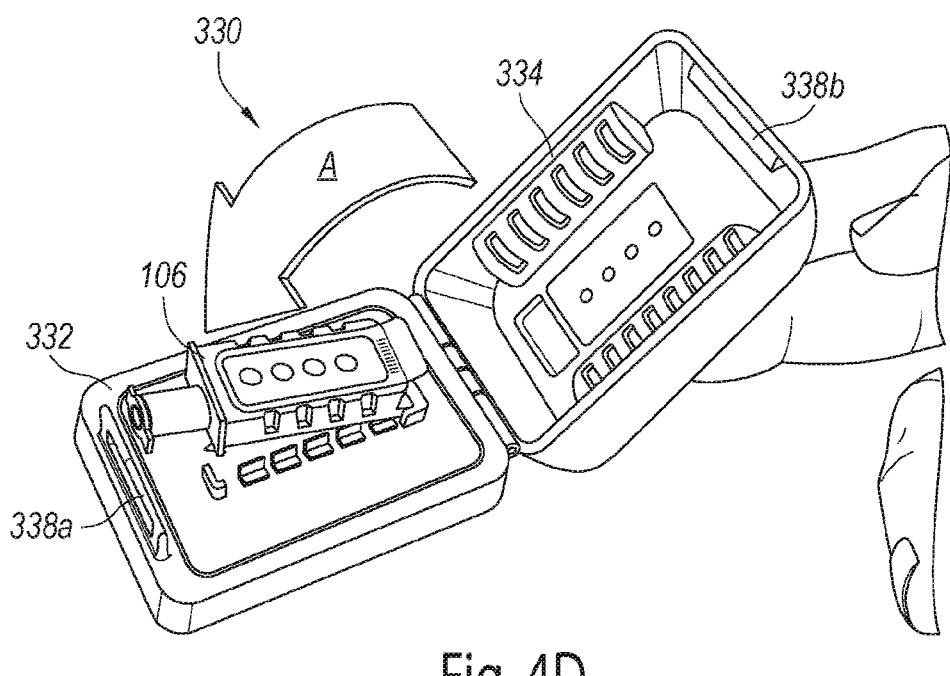
Figures 4E, 4F:
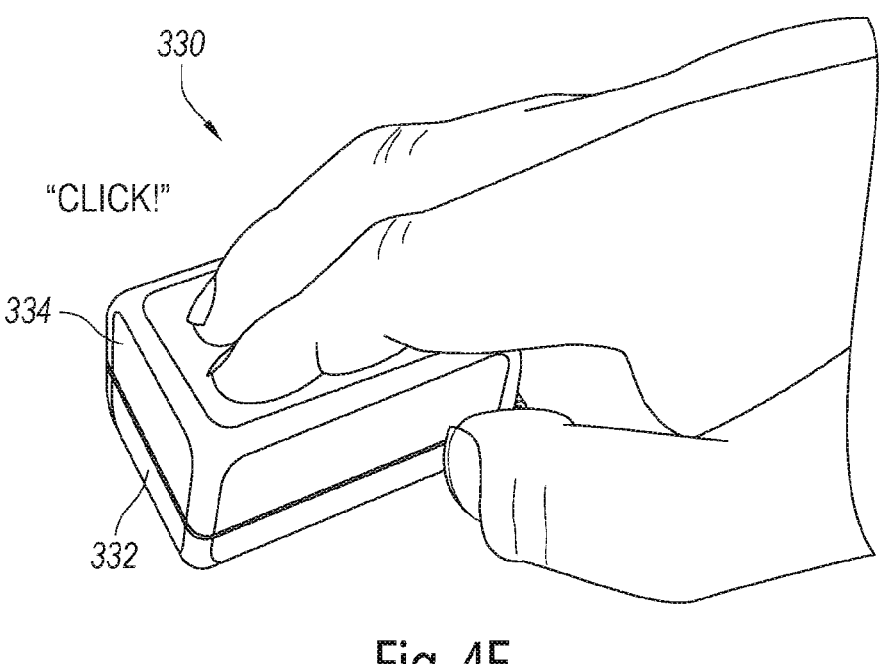

Then, referring to FIGS. 4D and 4E, the case 330 can be moved to the closed position. For example, the user can move the cover portion 334 of the case toward the base portion 332 in the direction indicated by the arrow A (or vis versa) until the snap lock portions 338 mate together to secure the case 330 in the closed position with the cartridge 106 positioned therein. The case 330 may be configured to provide an indication to the user when successfully closed (e.g., visual indicia, an audio signal, etc.) In some embodiments, moving the case 330 from the open position to the closed position pushes the cartridge 106 into the jig portion 340 to decouple the sample tray 112 from the housing 110. In other embodiments, the jig portion 340 can be omitted and the sample tray 112 can be decoupled from the housing 110 in other manners or need not be decoupled therefrom.

In some embodiments, referring to FIG. 4F, the user can attach a seal 450 to the case 330 across a portion of the base portion 332 and the cover portion 334. The seal 450 can inhibit the case 330 from being reopened and thus inhibit tampering and/or provide an indication that tampering has occurred. In some embodiments, the user can sign the seal 450 to authenticate/identify the sample collected within the case 330. In one aspect of the present technology, the seal 450 can facilitate tracing of the sample stored in the case 330.

Figure 4G:
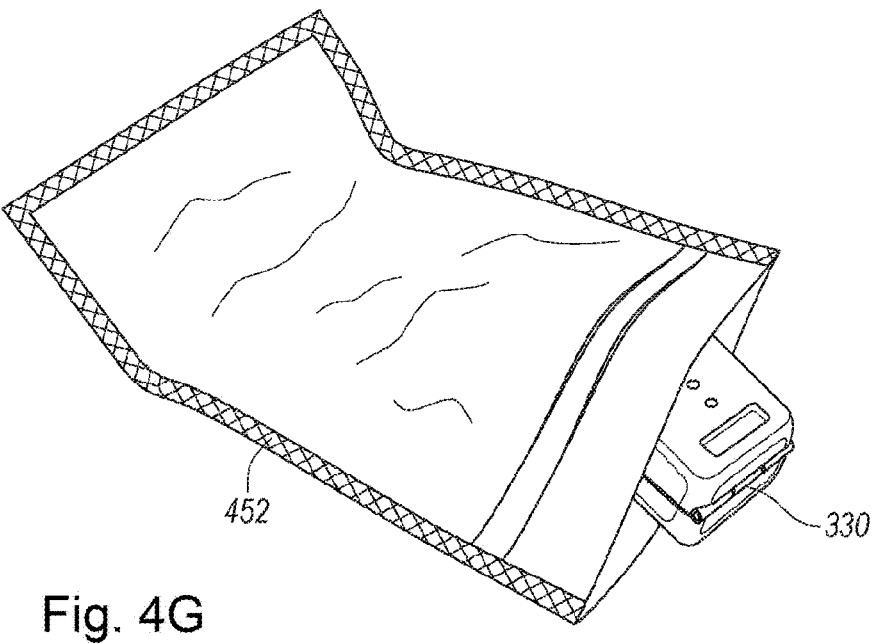
Figure 4H:
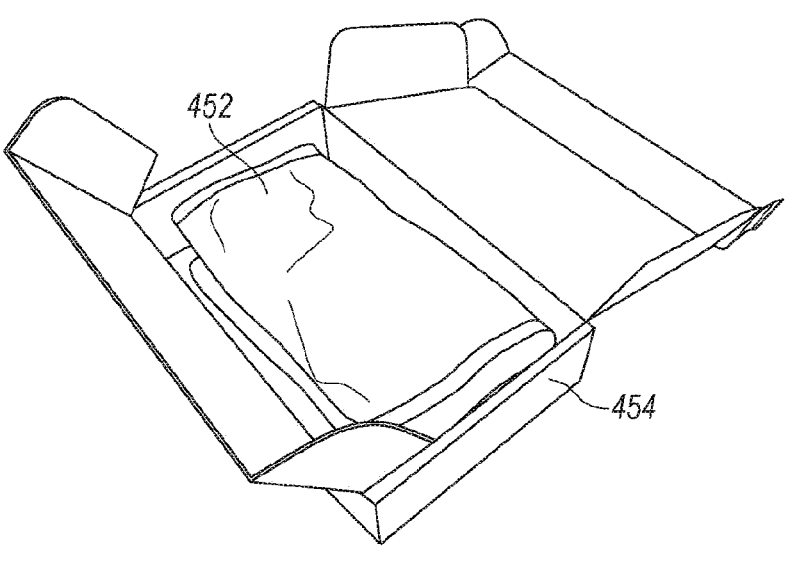

In some embodiments, referring to FIGS. 4G and 4H together, the case 330) can then be deposited into a sealed bag 452 (e.g., a snap-lock bag, zip-lock bag, press-lock bag, etc.) and the sealed bag 452 can be deposited into a shipping box 454. The box 454 can then be shipped to a testing facility or other location for further processing/evaluation. In other embodiments, the case 330 can be shipped in the sealed bag 452, without being deposited in another bag or box, or in other suitable matters.

In one aspect of the present technology, the case 330 enables the cartridge 106 and bodily fluid collected therein to be securely shipped while inhibiting contamination of the sample (e.g., from the external environment) and tampering with the cartridge 106.

Figure 5A:
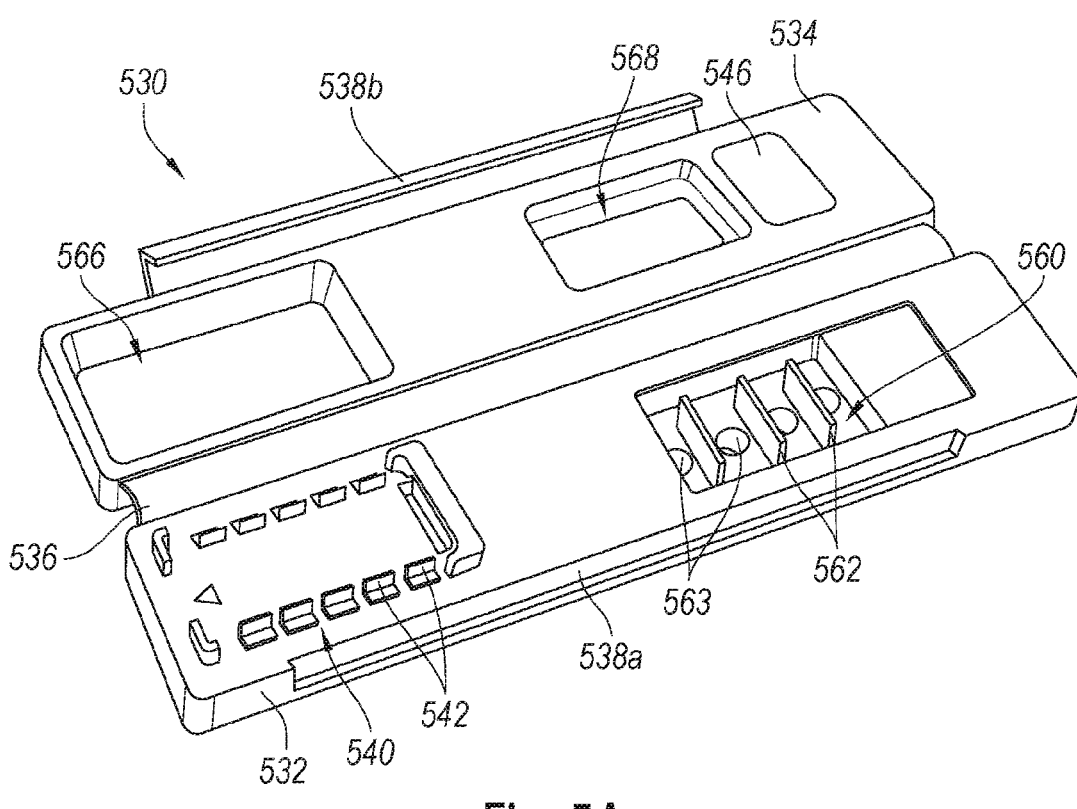
FIGS. 5A and 5B are isometric views of a case in an open position and a closed position, respectively, for securely storing and/or transporting the cartridge of FIGS. 1A-2B in accordance with additional embodiments of the present technology.
Figure 5B:
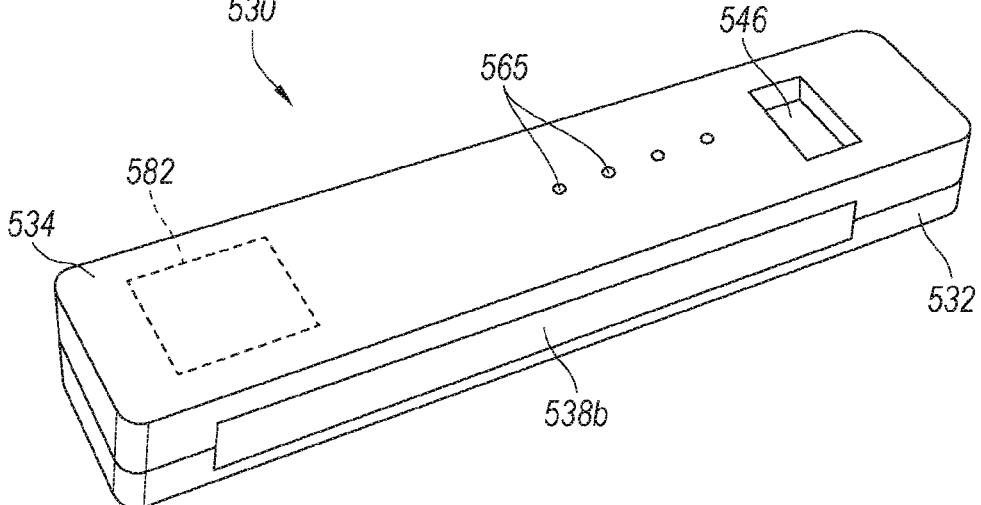

FIGS. 5A and 5B are isometric views of a case 530 in an open position and a closed position, respectively, for securely storing and/or transporting the cartridge 106 of FIGS. 1A-2B in accordance with additional embodiments of the present technology. Referring to FIGS. 5A and 5B together, the case 530 can include several features generally similar or identical to the features of the case 330 described in detail above with reference to FIGS. 3A and 3B. For example, in the illustrated embodiment the case 530 includes a base portion 532 and a cover portion 534 pivotally coupled to the base portion 532 via a hinge 536. In the open position shown in FIG. 5A, the cover portion 534 is pivoted away from the base portion 532 to, for example, allow the cartridge 106 to be inserted into the case 530. The base portion 532 and the cover portion 534 each include a snap lock portion 538 (identified individually as a first snap lock portion 538*a* and a second snap lock portion 538*b*) that mate/engage in the closed position to secure the cover portion 534 to/over the base portion 532. Moreover, the base portion 532 includes a jig portion 540 having a plurality of jig features 542 configured to (i) receive the cartridge 106 (FIGS. 1A-2B) and (ii) decouple the sample tray 112 of the cartridge 106 from the housing 110.

Referring to FIGS. 1A-2B, 5A, and 5B together, the base portion 532 can further include a sample receiving portion 560 (e.g., a recess, cavity, indentation, etc.) configured to receive the sample tray 112 of the cartridge 106 after it has been detached from the housing 110. In the illustrated embodiment, the sample receiving portion 560 includes a plurality of separators 562 (e.g., walls) positioned between corresponding ones of a plurality of first ports 563. The separators 562 are configured to separate (e.g., sealingly separate) adjacent ones of the collectors 228 of the sample tray 112 to, for example, inhibit fluid transfer between the collectors 228 when the sample tray 112 is positioned in/on the sample receiving portion 560. The cover portion 534 can include a plurality of second ports 565, and the first and second ports 563, 565 can be configured such that, when the sample tray 112 is in the sample receiving portion 560, the first and second ports 563, 565 are generally aligned with (e.g., are positioned above/below) (i) one another and (ii) the collectors 228 of the sample tray 112. A user, such as a lab technician, can remove (e.g., punch out) the collectors 228 by inserting a tool through corresponding ones of the first and second ports 563, 565. In some embodiments, the case 530 can include one or more puncturable sealing members (not shown) over the first and second ports 563, 565.

In the illustrated embodiment, the cover portion 534 includes a first recess 566 and a second recess 568 configured to be aligned over the jig portion 540 and the sample receiving portion 560 of the base portion 532, respectively, when the case 530 is in the closed position. When the case 530 is in the closed position, the housing 110 of the cartridge 106 can be positioned at least partially within the first recess 566 and the sample tray 112 can be positioned at least partially within the second recess 568. In some embodiments, the cover portion 534 can include a window 546 configured to be positioned at least partially over the sample receiving portion 560—and the sample tray 112 secured therein/thereto—when the case 530 is in the closed position. The window 546 can facilitate inspection of the cartridge 106. In some embodiments, the case 530 can further include a desiccant (not shown) positioned in/on the second recess 568 and/or the sample receiving portion 560 and configured to facilitate drying of bodily fluid collected in the sample tray 112. In some embodiments, the second recess 568 can include a plurality of posts (not shown: e.g., similar to posts 772 shown in FIGS. 7A-7D). Each of the posts can be configured (e.g., shaped and positioned) to be aligned, in the closed position, over (i) a corresponding one of the collectors 228 of the sample tray 112 and (ii) between an adjacent pair of the separators 562. Accordingly, when the cover portion 534 is moved to the closed position, the posts can engage the collectors 228 to eject/move the collectors 228 from the sample tray 112 and into the spaces between the separators 562.

FIGS. 6A-6H are isometric views of various stages in a method of using the case 530 to securely store and transport the cartridge 106 of Figures IA-2B in accordance with embodiments of the present technology. Although features of the method illustrated in FIGS. 6A-6H are described in the context of the case 530 and the cartridge 106 described in detail above with reference to FIGS. 1A-2B, 5A, and 5B, one skilled in the art will appreciate that the method can be practiced with other case designs and/or with other cartridge designs.

Figure 6A:
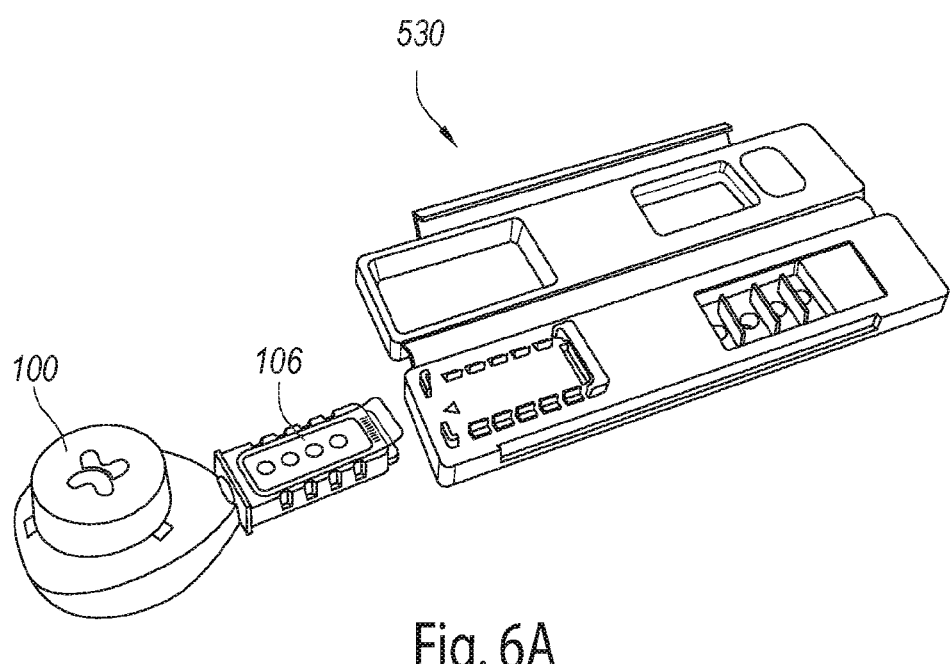
FIGS. 6A-6H are isometric views of various stages in a method of using the case of FIGS. 5A and 5B to securely store and transport the cartridge of FIGS. 1A-2B in accordance with embodiments of the present technology.
Figure 6B:
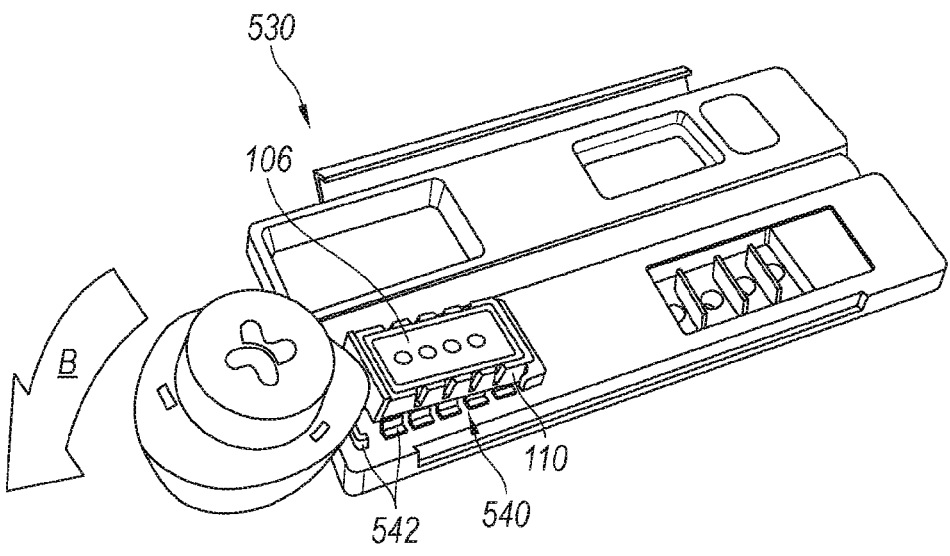

Referring first to FIG. 6A, the case 530 is moved to the open position after the device 100 is removed from a user when sufficient bodily fluid has been collected in the cartridge 106. Next, as shown in FIG. 6B, the cartridge 106 is positioned in/on the jig portion 540 of the case 530. Specifically, in some embodiments the housing 110 of the cartridge 106 can mate/engage with the jig features 542.

Figure 6C:
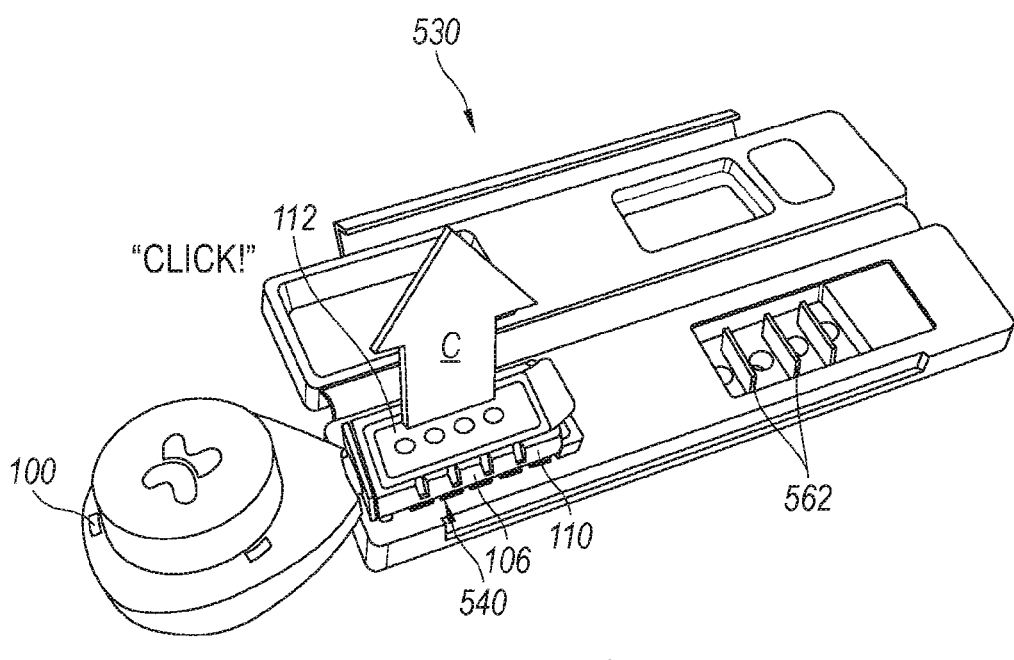

Referring to FIG. 6C, the cartridge 106 is then pushed/depressed into the jig portion 540 (e.g., in the direction indicated by arrow B in FIG. 6B) to decouple the sample tray 112 from the housing 110. In some embodiments, the device 100 can be rotated to engage the cartridge 106 with the jig portion 540. In other embodiments, the device 100 can first be detached from the cartridge 106, and then the cartridge 106 can be directly pressed against the jig portion 540. In other embodiments, the jig portion 540 can be omitted and the sample tray 112 can be decoupled from the housing 110 in other manners or need not be decoupled therefrom.

Figure 6D:
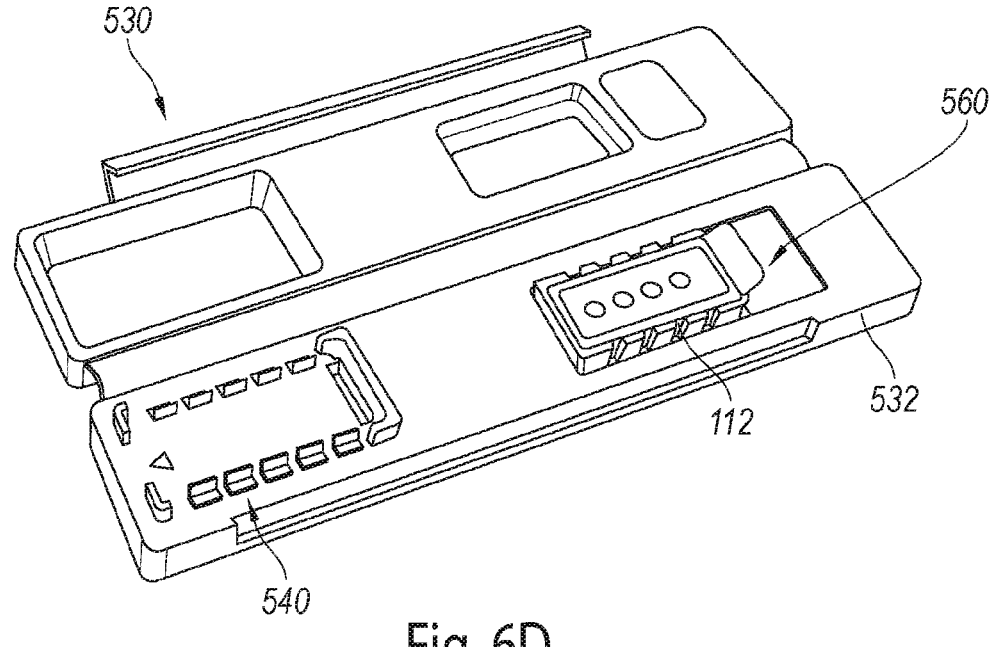

Next, referring to FIG. 6D, the sample tray 112 can be lifted away from the housing 110 (e.g., in the direction indicated by arrow C in FIG. 6C) and positioned in/on the sample receiving portion 560 of the base portion 532. When the sample tray 112 is positioned in the sample receiving portion 560, the separators 562 (obscured in FIG. 6D: shown in FIG. 6C) separate and/or seal the collectors 228 (obscured in FIG. 6D) from one another. In some embodiments, the housing 110 can be discarded after the sample tray 112 is detached therefrom. In other embodiments, the housing 110 can remain coupled to the jig portion 540.

Figure 6E:
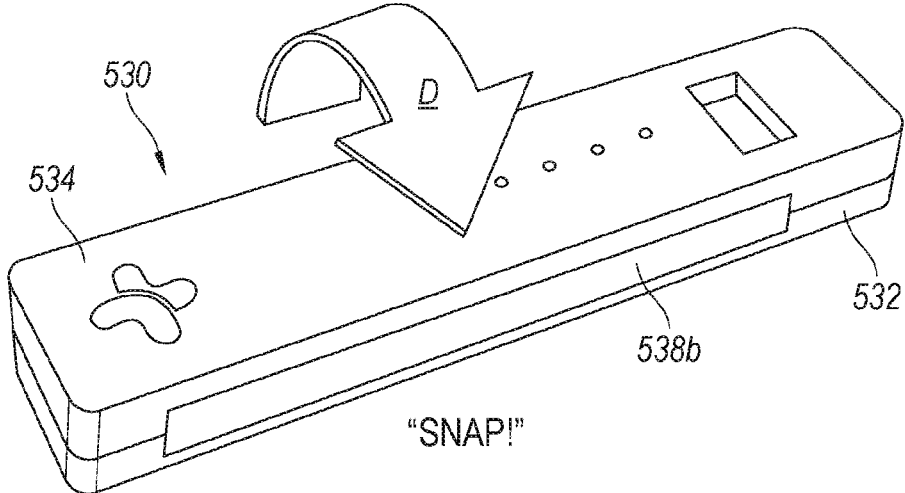
Figure 6F:
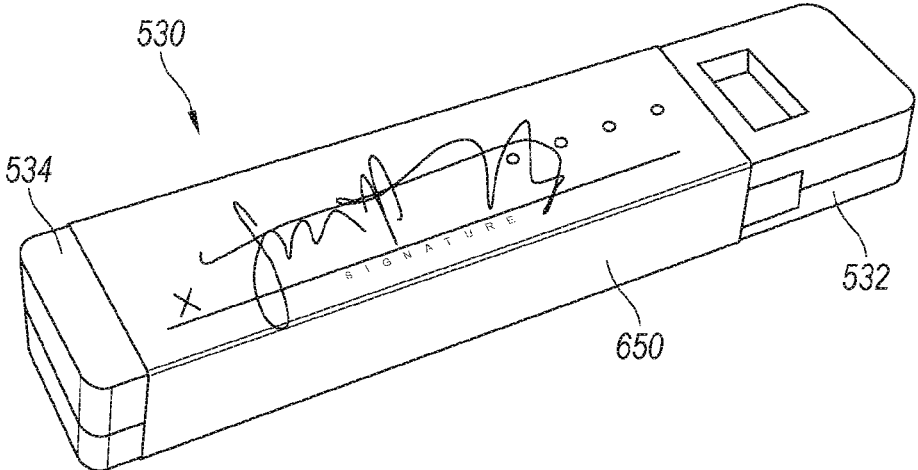

Referring to FIG. 6E, the case 530 can then be moved to the closed position. For example, a user (e.g., the patient, a technician, etc.) can move the cover portion 534 of the case toward the base portion 532 (e.g., in the direction indicated by the arrow D) until the snap lock portions 538 mate together to secure the case 530 in the closed position with the sample tray 112 positioned therein. As with the case 330 described above, the case 530 may also be configured to provide an indication to the user when successfully closed (e.g., visual indicia, an audio signal, etc.) In some embodiments, referring to FIG. 6F, the user can attach a seal 650 to the case 530 across a portion of the base portion 532 and the cover portion 534. The seal 650 can inhibit the case 530 from being reopened and thus inhibit tampering and/or provide an indication that tampering has occurred. In some embodiments, the user can sign the seal 650 to authenticate/ identify the sample collected within the case 530. In one aspect of the present technology, the seal 650 can facilitate tracing of the sample stored in the case 530.

Figure 6G:
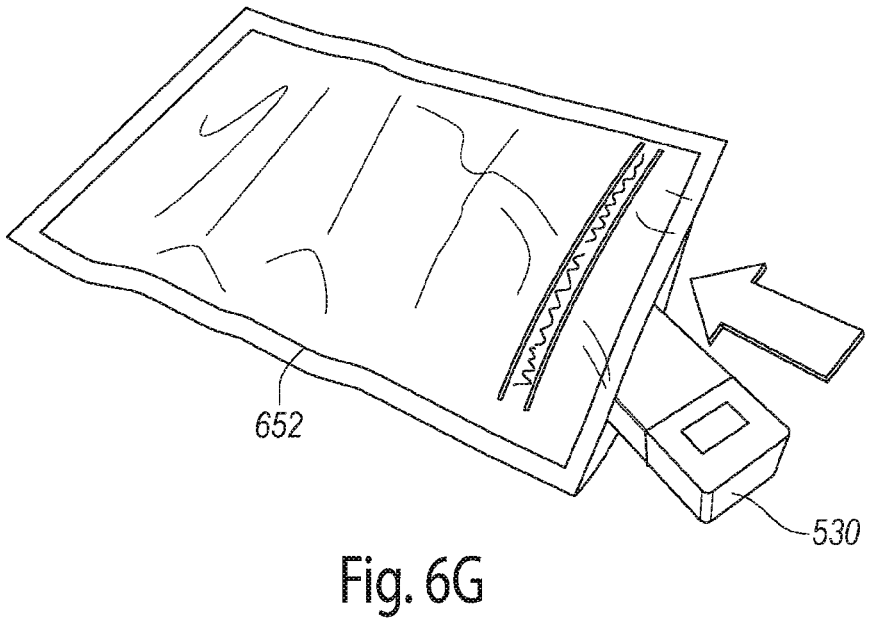
Figure 6H:
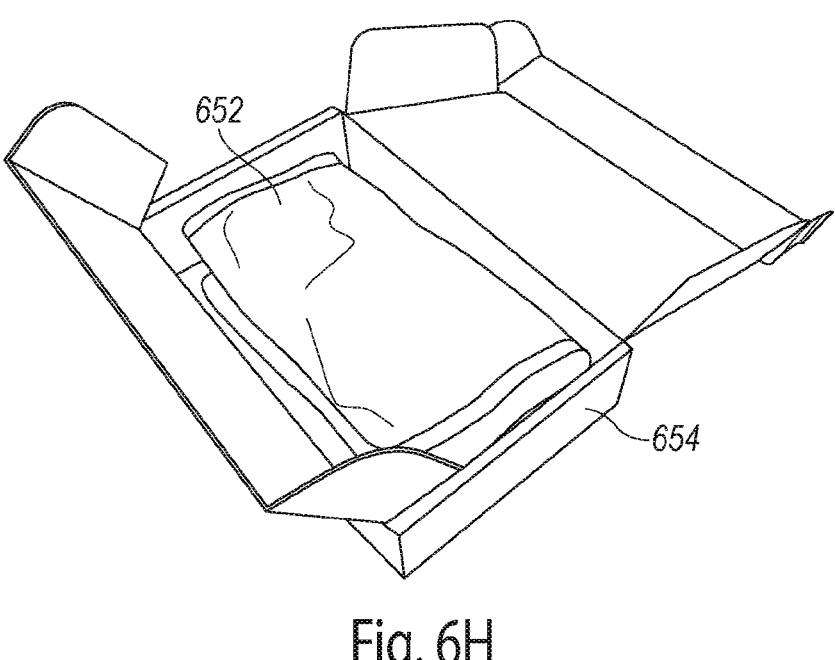

In some embodiments, referring to FIGS. 6G and 6H together, the case 530) can then be deposited in a sealed bag 652 (e.g., a snap-lock bag, zip-lock bag, press-lock bag, etc.) and the sealed bag 652 can be deposited in a shipping box 654. The box 654 can then be shipped to a testing facility or other location.

Referring to FIGS. 6A-6H together, in one aspect of the present technology the case 530 enables the sample tray 112 and bodily fluid collected therein to be securely shipped while inhibiting contamination of the sample (e.g., from the external environment) and inhibiting tampering with the cartridge 106. Moreover, the case 530 can inhibit cross-contamination between the samples collected in individual ones of the collectors 228 of the sample tray 112 by separating and/or sealing the collectors 228 from one another with the separators 562.

Figure 7A:
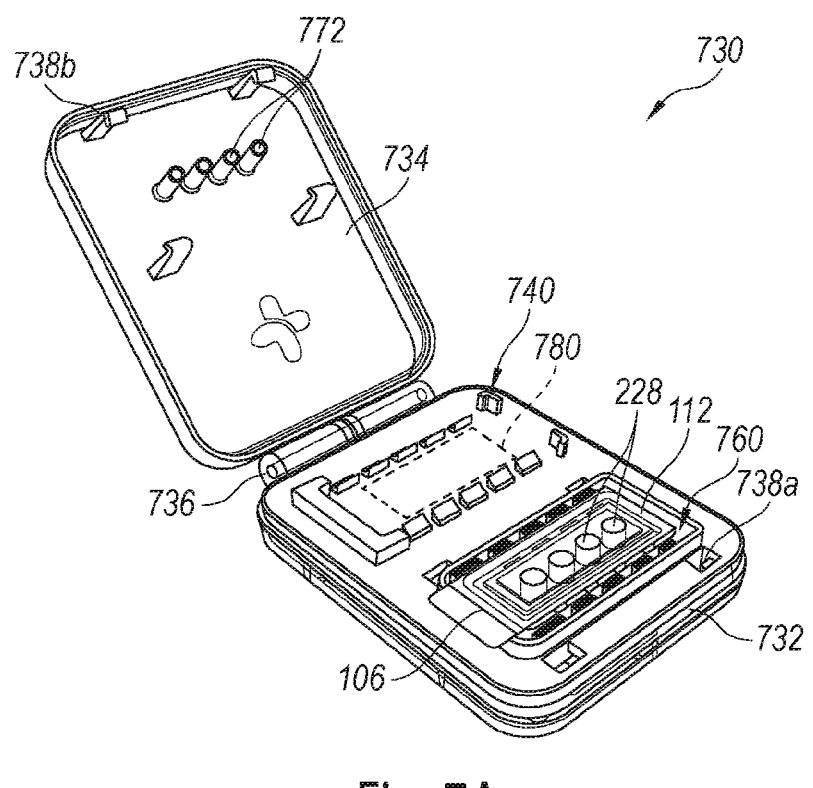
FIGS. 7A and 7B are isometric views of a case in an open position and a closed position, respectively, for securely storing and/or transporting the cartridge of FIGS. 1A-2B in accordance with additional embodiments of the present technology.
Figure 7B:
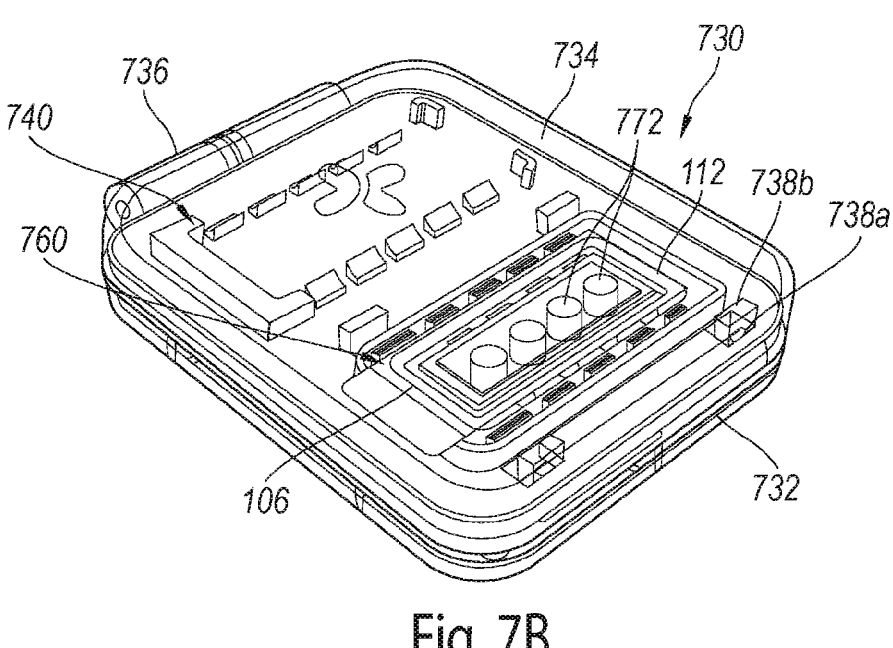
Figure 7C:
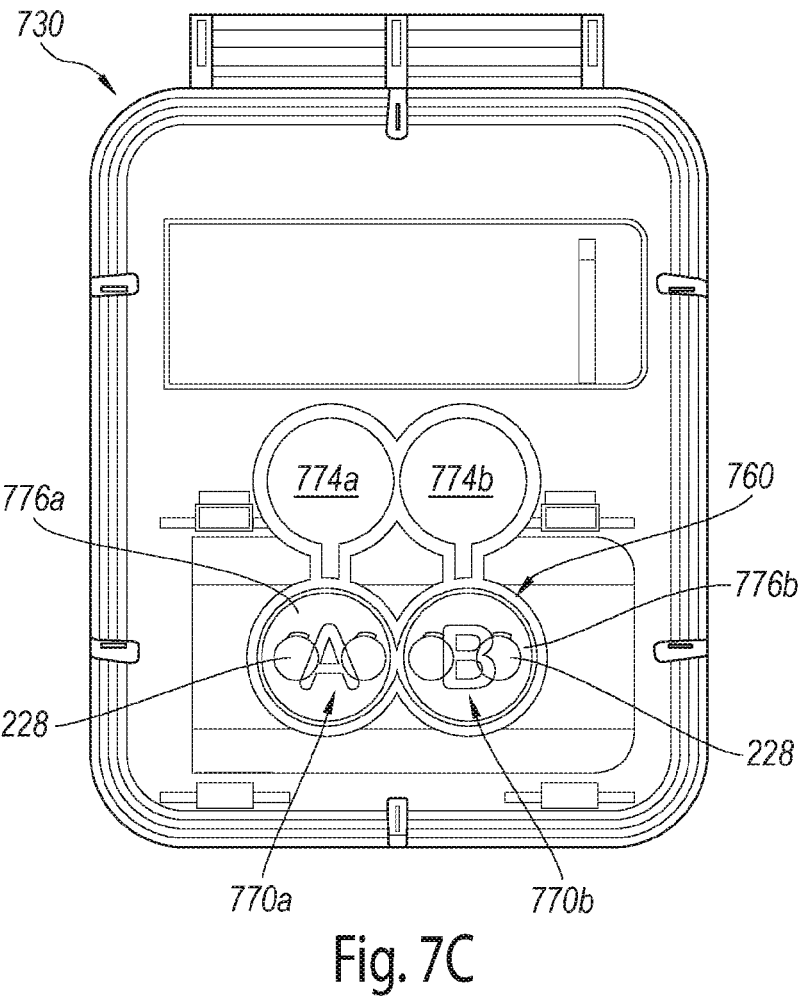
FIGS. 7C and 7D are a top view and a side view, respectively, of the case of FIGS. 7A and 7B in the closed position in accordance with embodiments of the present technology.
Figure 7D:
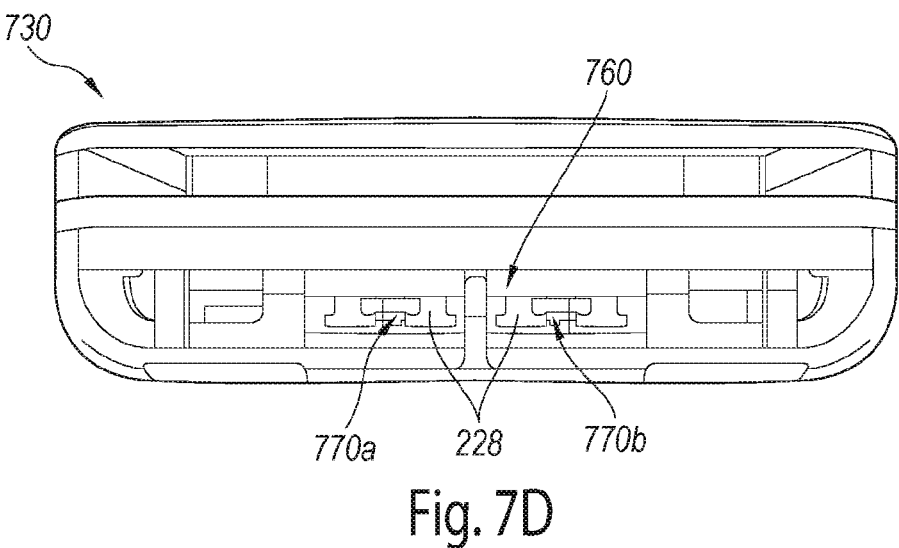

FIGS. 7A and 7B are isometric views of a case 730 in an open position and a closed position, respectively, for securely storing and/or transporting the cartridge 106 of FIGS. 1A-2B in accordance with additional embodiments of the present technology. FIGS. 7C and 7D are a top view and a side view, respectively, of the case 730 in the closed position in accordance with embodiments of the present technology. The sample tray 112 of the cartridge 106 is positioned in the case 730 in FIGS. 7A-7D.

Referring to FIGS. 7A and 7B together, the case 730 can include several features generally similar or identical to the features of the case 330 described in detail above with reference to FIGS. 3A-4H and/or the case 530 described in detail above with reference to FIGS. 5A-6H. For example, in the illustrated embodiment the case 730 includes a base portion 732 and a cover portion 734 pivotally coupled to the base portion 732 via a hinge 736. The base portion 732 and the cover portion 734 are shown as partially transparent in FIGS. 7A-7D for the sake of clarity. In the open position shown in FIG. 7A, the cover portion 734 is pivoted away from the base portion 732 to, for example, allow the cartridge 106 to be inserted into the case 730. The base portion 732 and the cover portion 734 each include a snap lock portion 738 (identified individually as a first snap lock portion 738a and a second snap lock portion 738b) that mate/engage in the closed position to secure the cover portion 734 to/over the base portion 732. In some embodiments, the snap lock portions 738 are configured to inhibit the case 730) from being reopened after closure, to thereby inhibit tampering with the sample tray 112 and/or provide an indication that tampering has occurred. Moreover, the base portion 732 includes a jig portion 740 configured to (i) receive the cartridge 106 and (ii) decouple the sample tray 112 of the cartridge 106 from the housing 110 (not shown in FIGS. 7A and 7B). In other embodiments, the jig portion 740 can be omitted and the sample tray 112 need not be decoupled from the housing 110 or can be decoupled in other manners.

In the illustrated embodiment, the base portion 732 further includes a sample receiving portion 760 (e.g., a recess, cavity, indentation, etc.) configured to receive the sample tray 112 of the cartridge 106 after it has been detached from the housing 110. Referring to FIGS. 7C and 7D together, the sample receiving portion 760 includes a pair of storage chambers 770 (identified individually as a first storage chamber 770a and a second storage chamber 770b) configured to be positioned below the sample tray 112 of the cartridge 106. In some embodiments, the storage chambers 770 are sealingly separated from another. In some embodiments, the case 730 can include one of the storage chambers 770 or more than two of the storage chambers 770.

Referring to FIGS. 7A-7D together, in the illustrated embodiment the cover portion 734 includes a plurality of posts 772 (e.g., pins, ejectors, etc.) extending therefrom. Each of the posts 772 is configured (e.g., shaped and positioned) to be aligned, in the closed position, over (i) a corresponding one of the collectors 228 of the sample tray 112 and (ii) one of the storage chambers 770. Accordingly, when the cover portion 734 is moved to the closed position, the posts 772 can engage the collectors 228 to eject/move the collectors 228 from the sample tray 112 and into either the first storage chamber 770a or the second storage chamber 770b positioned below the sample tray 112. FIGS. 7C and 7D illustrate the case 730 in the closed position and after two of the collectors 228 have been ejected from the sample tray 112 into each of the storage chambers 770. Accordingly, in one aspect of the present technology, the case 730 is configured to automatically remove the collectors 228 from the sample tray 112 via the engagement of the posts 772 with the sample tray 112 during closing of the cover portion 734. In another aspect of the present technology, the case 730 is configured to subdivide/partition the sample stored in the collectors 228 by isolating a first portion of the collectors 228 in the first storage chamber 770a and a second portion of the collectors 228 in the second storage chamber 770b.

Referring to FIG. 7C, in some embodiments the sample receiving portion 760 can include a first desiccant chamber 774a fluidly coupled to the first storage chamber 770a, and a second desiccant chamber 774b fluidly coupled to the second storage chamber 770b. The desiccant chambers 774 can include a desiccant (not shown) configured to facilitate drying of bodily fluid collected in the collectors 228. In other embodiments, the case 730 can include other substances, agents, etc., for producing a selected environment within the storage chambers 770. In some embodiments, the case 730 can include a first sealing member 776a over the first storage chamber 770a and a second sealing member 776b over the second storage chamber 770b. In some embodiments, the sealing members 776 can be foils, papers, plastics, etc. A user (e.g., a lab technician) can remove the sealing members 776 to access the storage chambers 770 and the collectors 228 stored therein. In some embodiments, the sealing members 776 can provide a visual indication that the case 730) has not been tampered with.

In some embodiments, a case configured in accordance with the present technology (e.g., the case 330, the case 530, and/or the case 730) can include electronic components integrated therein. Referring to FIG. 7A, for example, the case 730 can include electronic components 780 (shown schematically) integrated therein (e.g., into the base portion 732 and/or another portion of the case 730). The electronic components can include, for example, (i) radiofrequency identification (RFID) components (e.g., chips, receivers, transmitters) etc., for labeling and/or tracking the case, (ii) timing components for recording/stamping a time the case is closed, (iii) sample analysis components for analyzing a fluid sample collected in the cartridge 106, etc. In some embodiments, the case can further include a display (e.g., a digital readout) for displaying information generated/detected/collected by the electronic components. Referring to FIG. 5B, for example, the case 530) can include a display 582 (shown schematically) integrated therein (e.g., into the cover portion 534 and/or another portion of the case 530). The display can be configured to display (i) labeling information where the electronic components include RFID components, (ii) time stamp information where the electronic components include timing components. (iii) sample information where the electronic components include sample analysis components, etc. In some embodiments, the case can further include one or more input devices (e.g., buttons, touchscreens, etc.) configured to change the display.

In some embodiments, a case configured in accordance with the present technology (e.g., the case 330), the case 530, and/or the case 730) can be configured to process all or a portion of a sample collected in the cartridge 106. For example, the case can include plasma separation components (e.g., plasma separation paper) for separating plasma from whole blood collected within the collectors 228. Specifically, the case can be configured to fluidly couple the collectors 228 to one or more strips of plasma separation paper after they are removed/ejected from the sample tray 112. In some embodiments, the case can be configured to transfer liquid blood from the cartridge 106 onto any solid substrate. In such embodiments, the cartridge 106 can be configured to collect liquid blood. For example, the cartridge 106 can omit some or all of the collectors 228 and can instead include a liquid reservoir.

In some embodiments, a case configured in accordance with the present technology (e.g., the case 330, the case 530, and/or the case 730) can include components for inhibiting oxidation of a sample stored in the cartridge 106. For example, the case can include a vacuum source and/or can be coupled to an external vacuum source for generating a vacuum within the interior of the case when the case is closed. Alternatively or additionally, iron oxide and/or another suitable material can be positioned inside the case for capturing/removing oxygen therein.

In some embodiments, a case configured in accordance with the present technology (e.g., the case 330, the case 530, and/or the case 730) and/or packaging for shipping the case to a patient can include a unique QR code that is scannable by the patient via, for example, a smart phone or other mobile device. The QR code can be linked to a web portal or application that enables the patient to input information such as, for example, the time they use the device 100, identifying information, notes, etc. In some embodiments, scanning of the QR code can automatically indicate a time associated with when the device 100 is used by the patient to withdraw a sample of bodily fluid.

The following examples are illustrative of several embodiments of the present technology:

1. A device for storing a sample of bodily fluid collected in a sample tray of a collection cartridge, the device comprising:

a base including a jig portion, wherein the jig portion is configured to (a) receive the collection cartridge and (b) decouple the sample tray from a housing of the collection cartridge; and a cover pivotally coupled to the base, wherein the cover is movable relative to the base between an open position in which the jig portion is accessible and a closed position in which the jig portion is inaccessible.

2. The device of example 1 wherein the jig portion is configured to receive the housing of the collection cartridge, and wherein movement of the housing against the jig portion decouples the sample tray from the housing.

3. The device of example 1 or example 2 wherein— the sample tray includes a plurality of collectors configured to receive and store a portion of the bodily fluid:

the base includes a plurality of first ports extending therethrough:

the cover includes a plurality of second ports extending therethrough; and when the cover is in the closed position, individual ones of the first ports are configured to be aligned with (a) a corresponding one of the second ports and (b) a corresponding one of the collectors.

4. The device of any one of examples 1-3 wherein the base portion includes a sample receiving portion spaced apart from the jig portion, and wherein the sample receiving portion is configured to receive the sample tray.

5. The device of example 4 wherein the sample tray includes a plurality of collectors configured to receive and store a portion of the bodily fluid, and wherein the sample receiving portion includes a plurality of separators configured to be positioned between adjacent ones of the collectors when the sample receiving portion receives the sample tray.

6. The device of any one of examples 1-5, further comprising the sample tray.

7. A system for collecting and storing bodily fluid from a subject, the system comprising:

a collection device including an actuator operably coupled to a skin-piercing feature, wherein the bodily fluid collection device is configured to be positioned against the subject, and wherein the actuator is movable to move the skin-piercing feature at least partially into the subject to withdraw the bodily fluid;

a collection cartridge configured to be removably coupled to the collection device, wherein the collection cartridge includes a housing and a sample tray, and wherein the sample tray includes a plurality of collectors, and further wherein the collection cartridge is configured to receive the withdrawn bodily fluid and to store the withdrawn bodily fluid in at least one of the collectors; and a case including— a base including a jig portion, wherein the jig portion is configured to (a) receive the collection cartridge and (b) decouple the sample tray from the housing; and a cover pivotally coupled to the base, wherein the cover is movable relative to the base between a first position in which the jig portion is accessible and a second position in which the jig portion is inaccessible.

8. A method of collecting a sample of bodily fluid, the method comprising:

receiving the bodily fluid in a collector of a collection cartridge:

positioning the collecting cartridge against a jig portion of a case to decouple a tray portion of the collection cartridge from a housing of the collection cartridge, wherein the tray portion includes the collector; and closing a cover of the case such that the jig portion and collector are inaccessible.

9 The method of example 8, further comprising actuating a collection device fluidly coupled to the collection cartridge against skin of a subject to withdraw the bodily fluid from the subject into the collector.

10. The method of example 8 or example 9, further comprising:

positioning the case in a sealed bag; and shipping the sealed bag including the collector.

11. The method of any one of examples 8-10 wherein closing the cover moves the collection cartridge against the jig portion to decouple the tray portion from the housing.

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A system for collecting and storing bodily fluid from a subject, the system comprising:

a collection device including an actuator operably coupled to a skin-piercing feature, wherein the bodily fluid collection device is configured to be positioned against the subject, and wherein the actuator is movable to move the skin-piercing feature at least partially into the subject to withdraw the bodily fluid;

a collection cartridge configured to be removably coupled to the collection device, wherein the collection cartridge includes a housing and a sample tray, and wherein the sample tray includes a plurality of collectors, and further wherein the collection cartridge is configured to receive the withdrawn bodily fluid and to store the withdrawn bodily fluid in at least one of the collectors; and a case including:

a base including a jig portion, wherein the jig portion is configured to (a) receive the collection cartridge and (b) decouple the sample tray from the housing; and a cover pivotally coupled to the base, wherein the cover is movable relative to the base between a first position in which the jig portion is accessible and a second position in which the jig portion is inaccessible.

2. The system of claim 1, wherein the jig portion is configured to receive the housing of the collection cartridge, and wherein movement of the housing against the jig portion decouples the sample tray from the housing.

3. The system of claim 1, wherein:

the base includes a plurality of first ports extending therethrough;

the cover includes a plurality of second ports extending therethrough; and when the cover is in the second position, individual ones of the first ports are configured to be aligned with (a) a corresponding one of the second ports and (b) a corresponding one of the collectors.

4. The system of claim 1, wherein the base includes a sample receiving portion spaced apart from the jig portion, and wherein the sample receiving portion is configured to receive the sample tray.

5. The system of claim 4, wherein the sample receiving portion includes a plurality of separators configured to be positioned between adjacent ones of the collectors when the sample receiving portion receives the sample tray.

6. The system of claim 1, wherein the jig portion includes a plurality of discrete jig features that are spaced apart and are arranged in a pattern along a top surface of the jig portion and are spaced inward from a peripheral edge of the base.

7. The system of claim 1, wherein the housing of the collection cartridge includes a pair of outer sidewalls and a pair of inner sidewalls with a fluid channel being defined between the inner sidewalls, the plurality of collectors being disposed between the pair of inner sidewalls within the fluid channel.

8. The system of claim 7, wherein the sample tray includes a pair of sidewalls that abut and are disposed along outer surfaces of the pair of outer sidewalls, the plurality of collectors being disposed between the pair of sidewalls of the sample tray, the sample tray being securely coupled to the housing of the collection cartridge by one or more mating features.

9. The system of claim 1, wherein the jig portion comprises a plurality of jig features formed along an upper surface of the base, the base further including a plurality of first ports extending therethrough and formed between the plurality of jig features.

10. The system of claim 9, wherein the cover includes a plurality of second ports extending therethrough; and when the cover is in the second position, individual ones of the first ports are configured to be aligned with (a) a corresponding one of the second ports and (b) a corresponding one of the collectors.

11. The system of claim 1, wherein the case further includes one or more desiccants positioned in/on the cover and/or the base.

12. The system of claim 11, wherein the one or more desiccants comprise a plurality of desiccants that are located along sides of the cover with a plurality of second ports being located between the plurality of desiccants.

13. The system of claim 10, wherein the plurality of second ports are located inward from an outer periphery of the cover.

14. A system for collecting and storing bodily fluid from a subject, the system comprising:

a collection device configured to withdraw the bodily fluid;

a collection cartridge configured to be removably coupled to the collection device, wherein the collection cartridge includes a housing and a sample tray; and a case including:

a base including a jig portion, wherein the jig portion is configured to (a) receive the collection cartridge and (b) decouple the sample tray from the housing; and a cover pivotally coupled to the base, wherein the cover is movable relative to the base between a first position in which the jig portion is accessible and a second position in which the jig portion is inaccessible.

* * * * *